United States Patent [19]
Irikura et al.

[11] Patent Number: 5,151,434
[45] Date of Patent: Sep. 29, 1992

[54] CONTROLLED-RELEASE COMPOSITION AND THE PREPARATION THEREOF

[75] Inventors: Tsutomu Irikura, Tokyo; Hirohsi Uchida, Saitama; Jun Imai, Kanagawa; Masakatsu Komuro, Tochigi, all of Japan

[73] Assignee: Kyorin Seiyaku Kabushiki Kaisha, Tokyo, Japan

[21] Appl. No.: 448,889

[22] Filed: Dec. 12, 1989

Related U.S. Application Data

[63] Continuation of Ser. No. 143,225, Jan. 6, 1988, abandoned, which is a continuation of Ser. No. 711,031, Mar. 12, 1985, abandoned.

[30] Foreign Application Priority Data

Mar. 14, 1984 [JP] Japan .................................. 59-48441

[51] Int. Cl.$^5$ .............................................. A61K 31/44
[52] U.S. Cl. ..................... 514/300; 514/929; 514/964
[58] Field of Search ....................... 514/300, 929, 964

[56] References Cited

U.S. PATENT DOCUMENTS 4,540,566 9/1985 Davis et al. ............................ 424/22
4,548,490 10/1985 Mueller et al. ......................... 525/13

FOREIGN PATENT DOCUMENTS 1378375 12/1974 United Kingdom .

OTHER PUBLICATIONS

Chemical Abstracts 93:155800e (1980).

Primary Examiner—Leonard Schenkman
Attorney, Agent, or Firm—McAulay Fisher Nissen Goldberg & Kiel

[57] ABSTRACT

A controlled-release pharmaceutical preparation of 3-isobutyryl-2-isopropylpyrazolo[1,5-a]pyridine. The controlled-release preparation is in the form of powder or granule containing 3-isobutyryl-2-isopropylpyrazolo[1,5-a]pyridine, coated with medically non-active substance or in the form of rectal suppository containing 3-isobutyryl-2-isopropylpyrazolo[1,5-a]pyridine. Further the controlled-release is prepared by implanting 3-isobutyryl-2-isopropylpyrazolo[1,5-a]pyridine in fatty materials, or granulating it and coating the resultant particles with medically non-active substance.

9 Claims, 3 Drawing Sheets

CONTROLLED-RELEASE COMPOSITION AND THE PREPARATION THEREOF

This is a continuation of application Ser. No. 07/143,225, filed Jan. 6, 1988, which, in turn, is a continuation of application Ser. No. 06/711,031, filed Mar. 12, 1985, both now abandoned.

BACKGROUND OF THE INVENTION

Field of the Invention

This invention relates to pharmaceutical preparations containing a controlled-release of 3-isobutyryl-2-isopropylpyrazolo[1,5-a]pyridine (Code No. KC-404), and production methods thereof.

Description of the Prior Art

KC-404, the molecular weight being 230.0, has a chemical structure as described below. It is a white crystalline powder having a melting point of 51°–54° C., and well soluble in chloroform and ethanol, but almost insoluble in water.

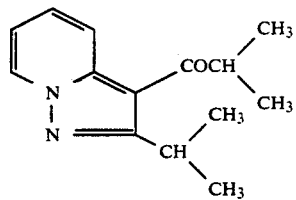

KC-404 is a therapeutically useful compound having a cerebral vasodilating and bronchodilating action as disclosed in U.S. Pat. No. 3,850,941 corresponding to Japanese Patent Publication No. 52-29318.

SUMMARY OF THE INVENTION

Nausea and vomiting were, however, caused by KC-404 when orally taken as bulk powder. Development of the side effects seemed to be associated with the sudden increase of KC-404 serum concentration, because they developed in the early stage just after the dose was given and not at a later stage, and the time of development coincided with that of the initial increase in the serum concentration. It is therefore an important object of this invention to develop well controlled-release preparations and production methods thereof, to control the sudden increase of serum concentration.

This invention provides granules, fine granules, capsules, tablets and rectal suppositories as therapeutically useful controlled-release preparations of KC-404.

Various pharmaceutical procedures have been proposed for controlling the release rate of medicaments in the form of an oral dosage. In the preparation of controlled-release dosage forms of KC-404, various procedures had been conducted such as the mixing of crystalline powders of different particle sizes having different dissolution rates, coating of the powders or granules containing KC-404 with various coating materials and implantation of the KC-404 into a matrix such as wax, however, the film coating technique is the most suitable for the oral preparation of this invention. As a base for rectal suppositories, oleaginous bases were the most suitable for controlled-release suppositories of KC-404 among water soluble, oleaginous and emulsion-type bases.

DETAILED DESCRIPTION OF THE INVENTION

In terms of the polymeric coating agents for covering the surfaces of solid particles, pharmaceutically usable polymeric substances can be employed, such as Eudragit Retard ® (copolymer of ethyl methacrylate and trimethylacrylethylammonium chloride, Röhm Pharma Co., Ltd.), Eudragit L ® (copolymer of methyl methacrylate and methacrylate, Röhm Pharma Co., Ltd.), Eudragit S ® (copolymer of methyl methacrylate and methacrylate, Röhm Pharma Co., Ltd.) as an acrylate polymer, Ethocel ® (ethylcellulose, Dow Chemical Co., Ltd.), Metolose ® (methylcellulose, Shinetsu Kagaku Co., Ltd.), HPMCP ® (hydroxypropylmethylcellulose phthalate, Shinetsu Kagaku Co., Ltd.), and (hydroxypropylmethylcellulose acetate succinate, Shinetsu Kagaku Co., Ltd.) as a cellulose derivative, and the mixtures thereof.

The granules containing KC-404 are prepared by a standard procedure using pharmaceutically available excipients such as lactose, starch, Avicel ® (crystalline cellulose, FMC Corp.) and mannitol as a filler, HPC-L ® (hydroxypropylcellulose, Nippon Soda Co., Ltd.), PVP (polyvinylpyrrolidone) and starch paste as a binder. The granules can also be produced by spray-coating ethanol solution containing KC-404 onto inert granules, preferably of a spherical shape, prepared with lactose, starch, Avicel ® and others in a fluidized bed apparatus such as Spiracola ®. These conventional granules are converted to controlled-release granules having different degrees of dissolution rates by coating an appropriate solution or suspension of a foregoing polymer or the mixture thereof in water, ethanol or other solvents. The controlled-release granules or their mixture are formed as capsules or tablets in a usual manner with suitable excipients such as lactose and starch. The controlled-release tablet of KC-404 can also be produced by coating a conventional tablet consisting of usual ingredients such as lactose, starch and Avicel ® with a foregoing polymer or the mixture thereof.

Oleaginous bases like cocoa butter and water soluble bases like polyethylene glycol can be utilized to produce suppositories, but oleaginous bases are the most suitable for controlled-release suppositories of this invention. As the oleaginous base, cocoa butter, Witepsol ® hard fat (Dynamite Novel Co., Ltd.), Novata ® hard fat (Henkel Hakusui Co., Ltd.), plant oils, animal fats and fatty acids and a mixture thereof can be used. In accordance with this invention, the controlled-release suppositories can be prepared by cooling the melted mixture of KC-404 and the bases in a plastic container for suppositories, or by formulating the KC-404 solution in plant oil into soft rectal capsules.

The controlled-release granules produced in this invention showed slower dissolution in comparison with the bulk powder as illustrated in FIG. 1 (controlled-release granules), and FIG. 2 (mixed controlled-release granules), when tested according to the dissolution test of JP10, the First Method (rotating basket). The dissolution test was conducted as follows. Apparatus: JP10, rotating basket (100 mesh of openings) methods, a rotation speed of 100 rpm and the temperature at $37 + 0.5°$ C. Test fluid: 500 ml each of the First and Second Medium for the disintegration test of JP10. Test time: 2 hrs. in the First Medium and subsequent time in the Second Medium unless specified otherwise. Specimen: granules equivalent to 20 mg of KC-404. Assay: spectrophotometric determination at 319 nm.

Oral absorption and the development of side effects were investigated with controlled-release granules obtained in this invention by healthy volunteers in some instances. As shown in FIGS. 3 and 4, the controlled-release granules exhibited a more gradual increase in the serum level and sustaining level than that of the bulk powder. The volunteer test was performed as follows. Administration: oral administration of granules equivalent to 10 or 20 mg of KC-404, and rectal administration of suppositories containing 20 mg of KC-404. Assay: mass-fragmentography.

The controlled-release oral preparation of this invention displayed a lower frequency of side effects such as nausea and vomiting (0/132: dose frequency times volunteer number) as compared to 3/6 of the bulk powder. As shown in FIG. 5, the controlled-release suppositories of KC-404 produced in this invention using oleaginous bases exhibited a gradual increase in the serum level to 6 hrs. and maintained the level up to at least 15 hrs. after the dose was given to the healthy volunteers. This suppository was of a very safe dosage, as there was no development of nausea or vomiting in three subjects.

The invention will be described in greater detail in conjunction with the following specific examples, but the invention should not be regarded as being limited thereto.

DETAILED DESCRIPTION OF THE PREFERRED EMBODIMENTS

Example 1

Figure 1:
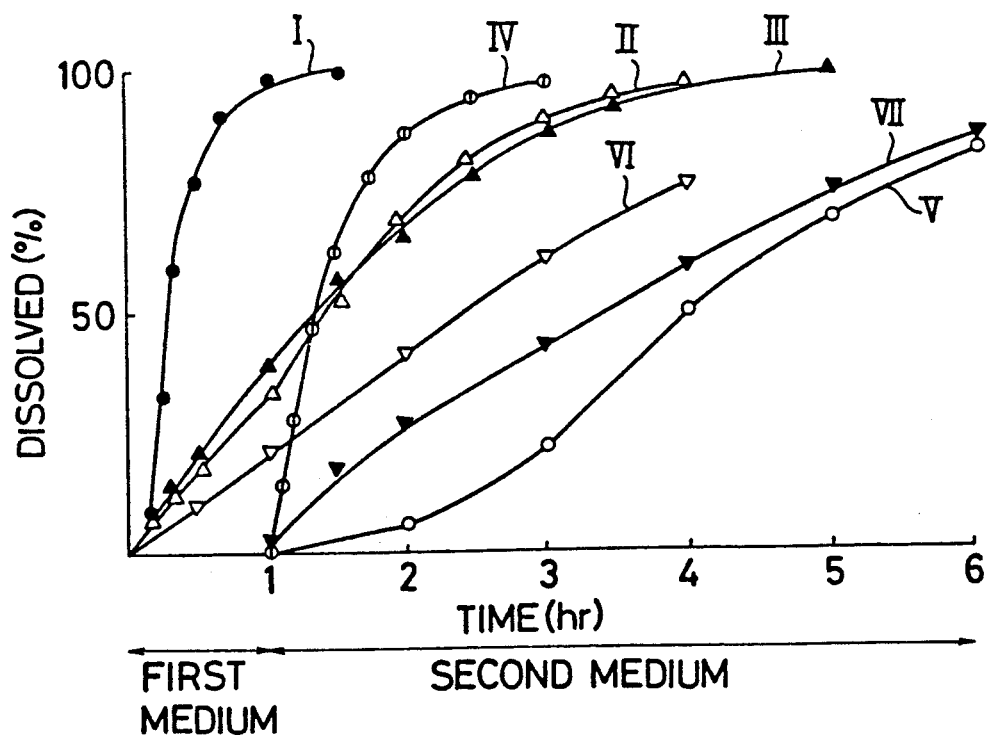
FIG. 1 illustrates the dissolution of controlled-release granules prepared in this invention. I, II, III, IV and V in the figure represent bulk powder of KC-404, controlled-release granules of Example 1, controlled-release granules of Example 2, enteric-coated granules of Example 4 and enteric-coated controlled-release granules of Example 3, respectively. VI and VII in the figure also represent controlled-release granules of Example 5 and enteric-coated controlled-release granules of Example 6, respectively.
Figure 3:
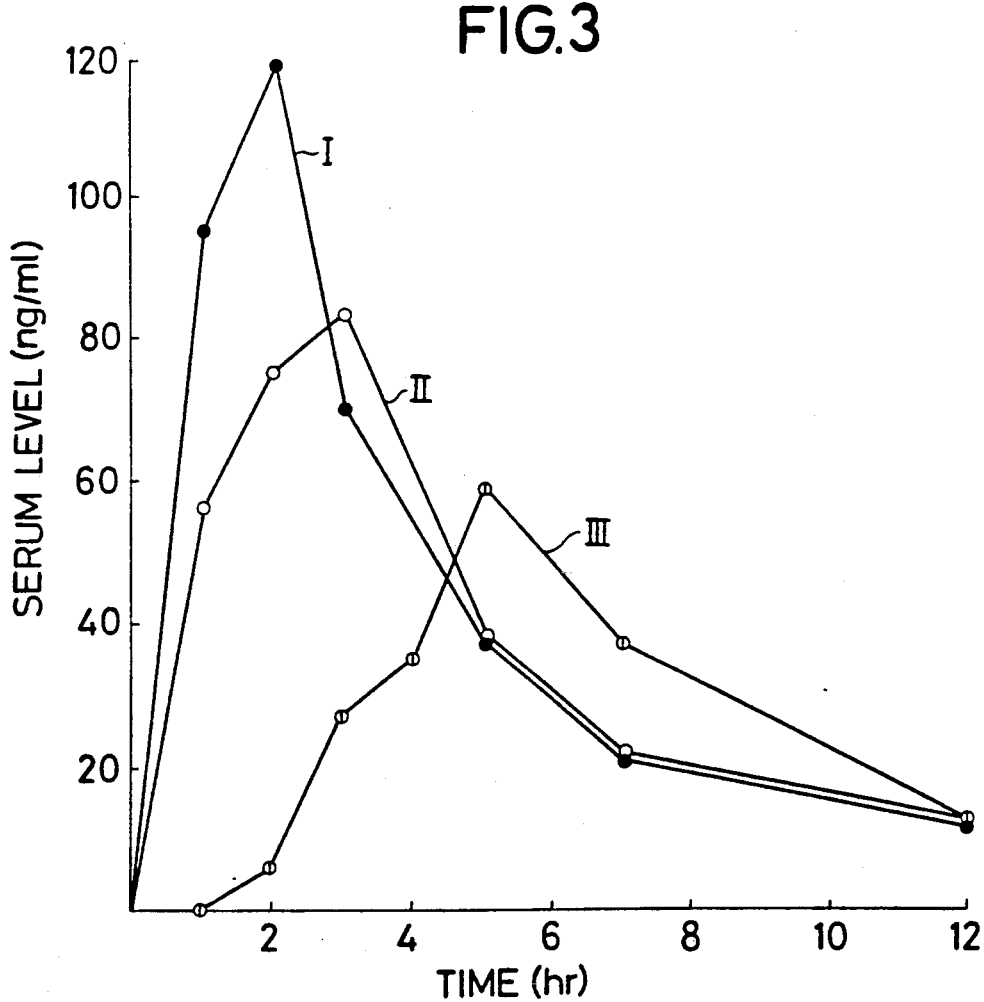
FIGS. 3 and 4 illustrate the serum level profiles in healthy volunteers who received bulk powder or preparations produced in the present invention, equivalent to 20 mg of KC-404 except in the case of VI (10 mg of KC-404). I, II and III in FIG. 3 represents bulk powder, controlled-release granules of Example 1 and enteric-coated granules of Example 4, respectively. IV, V and VI in FIG. 4 represents the mixed-granule preparation of Examples 7, 8 and 9, respectively.

A mixture of 4800 g of lactose and 1200 g of Avicel ® was kneaded with 1800 g of 2.5 % aqueous solution of HPC-L. The resulting moist mass was granulated and dried to produce a core granule having a diameter of 0.5–0.71 mm. Onto the core granules thus obtained, 3000 g of ethanol solution containing 200 g of KC-404 and 40 g of Eudragit L ® was sprayed in a fluidized bed coating apparatus (Spiracota ®)) to form a conventional granule. 1900 g of the conventional granule was coated with 580 g of 3.3 % ethanol solution of Eudragit Retard S ® the same apparatus to prepare a controlled-release granule. The controlled-release granule showed about 70 % dissolution in the First Medium at 2 hrs. (II of FIG. 1) and a slower increase of the serum level in comparison with that of the bulk powder when capsules containing granules equivalent to 20 mg of KC-404 were taken by healthy volunteers (II of FIG. 3).

Example 2

To 20 kg of the core granules, prepared as Example 1, 29.2 kg of 8.6% ethanol solution of KC-404 was sprayed in the Spiracota ®. The resulting granule 24 kg was coated with 3 % ethanol solution of Eudragit Retard S ® to form a controlled-release granule. The controlled-release granule provided about 67 and 96% dissolution at 2 and 4 hrs. (III of FIG. 1).

Example 3

To 500 g of the controlled-release granule of Example 2, 1500 g of 3.3% ethanol solution of Eudragit S ® was sprayed in Spiracota ® to prepare an enteric-coated controlled-release granule. The resulting granule exhibited about 2% dissolution in the First Medium at 1 hr. and about 21% and 69% dissolution in the Second Medium at the subsequent 3 and 5 hrs., respectively (V of FIG. 1).

Example 4

To 500 g of the conventional granule, prepared as Example 1, 5% ethanol solution of Eudragit L ® was sprayed in Spiracota ® to produce an enteric-coated granule. The resulting granule showed about 4% dissolution in the First Medium at 1 hr. and 87% dissolution in the Second Medium at the subsequent 1 hr. (IV of FIG. 1). The serum level in healthy volunteers due to this granule displayed a lag time of absorption and attained a peak at about 5 hrs. after the dose (20 mg of KC-404) was given and more sustaining curve existed in comparison with that of the bulk powder, as shown as III of FIG. 3.

Example 5

A mixture of 22.5 kg of lactose and 7.5 kg of crystalline cellulose ) was blended with 11.0 kg of 2% aqueous solution of polyvinylpyrrolidone K-90. The resultant mass was granulated, screened and dried to prepare a core granule having a diameter of about 0.5–0.7 mm. 12 kg of core granules thus prepared were sprayed with 9 kg of 8.3% ethanol solution of KC-404 in a fluidized bed coating apparatus to produce a conventional granule. 4 kg of the resulting granule was converted to a controlled-release granule by spraying 3.2 kg of 3.3% ethanol solution of Eudragit Retard S ®. The controlled-release granule exhibited about 75% dissolution at 4 hrs. (VI, of FIG. 1).

Example 6

To 3 kg of the controlled-release granule of Example 5, 4.2 kg of 3.3% ethanol solution of Eudragit L ® was sprayed in a fluidized bed coating apparatus to form an enteric-coated controlled-release granule. The resulting granule showed 4% dissolution in the First Medium at 1 hr. and about 75% dissolution in the Second Medium at the subsequent 4 hrs. VII of FIG. 1).

Example 7

Figure 2:
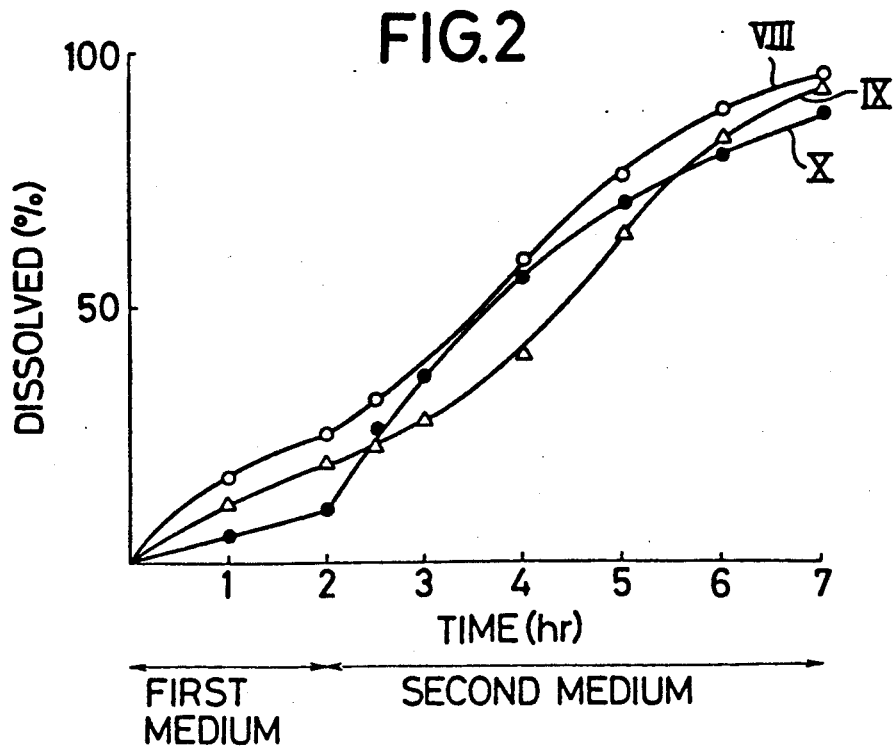
FIG. 2 represents the results of the dissolution test of various mixed-granule preparations. VIII, IX and X in the figure represents the mixed-granule preparation of Examples 7, 8 and 9, respectively.
Figure 4:
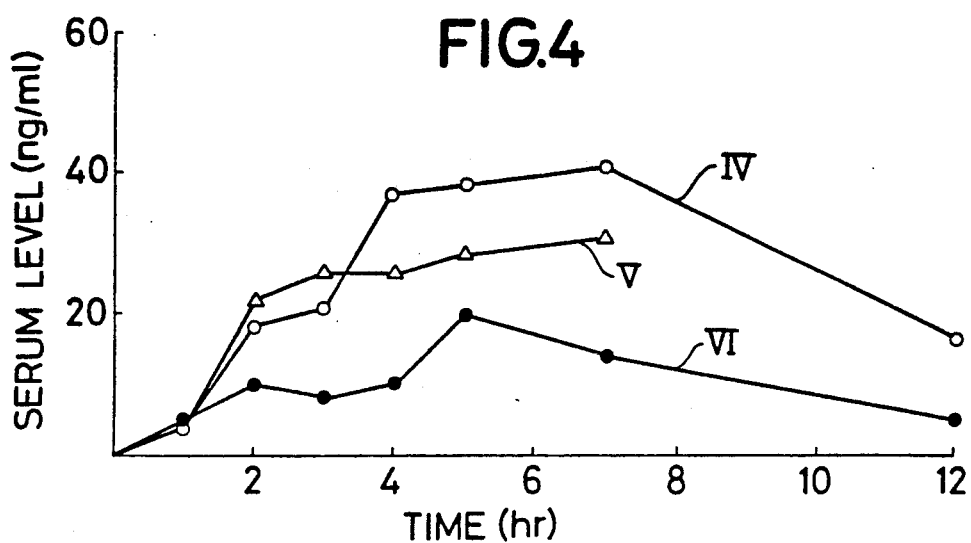

A mixed-granule preparation was produced by blending a part of the controlled-release granule of Example 1 and 2 parts of the enteric-coated controlled-release granule of Example 3, whereby "a part" refers to a weight of the granule equivalent to the amount of KC-404. The same definition will be utilized hereinafter. The resulting mixed-granule preparation showed about 25% dissolution in the First Medium at 2 hrs. and about 78% dissolution in the Second Medium at the subsequent 3 hrs. (VIII of FIG. 2). The mixed-granule preparation exhibited a more prolonged serum level as compared with that of the bulk powder, having a gradual increase up to 4 hrs. and a peak level at 7 hrs. after the dose (20 mg of KC-404) was given (IV of FIG. 4).

Example 8

A mixed-granule preparation was produced by blending a part of the controlled-release granule of Example 2 and 3 parts of the enteric-coated controlled-release granule of Example 3. The resulting preparation showed about 20% dissolution in the First Medium at 2 hrs. and 65% dissolution in the Second Medium at the subsequent 3 hrs. (IX of FIG. 2). The serum level obtained with this preparation (20 mg of KC-404) indicated a more gradual absorption and as compared with the bulk powder (V of FIG. 4), a more sustained serum level in the healthy volunteers was obtained as well.

Example 9

A mixed-granule preparation was prepared by blending a part of the controlled-release granule of Example 5 and 3 parts of the enteric-coated controlled-release granule of Example 6. The resulting preparation exhibited about 10% dissolution in the First Medium at 2 hrs. and about 70% dissolution in the Second Medium at the subsequent 3 hrs. (X of FIG. 2). The mixed-granule preparation was put into hard capsules of 10 mg of KC-404. The capsule provided the gradual increase in the serum level up to 5 hrs. and attained a peak at 5 hrs. after the dose was given (VI of FIG. 4).

Example 10

A mixture of 100 g of KC-404, 625 g of mannitol, 100 g of Avicel ® and 150 g of potato starch was kneaded with 200 g of 2.5% aqueous solution of HPC-L ®, and was then granulated, screened and dried in a usual manner to form a conventional granule having a diameter of 0.5–0.7 mm. 500 g of the resulting granule was spray-coated with 600 g of 3.3% ethanol solution of Eudragit Retard S ® to prepare a controlled-release granule. The controlled-release granule showed about 20% dissolution in the First Medium at 2 hrs. and about 70% dissolution in the Second Medium at the subsequent 5 hrs.

Example 11

To 1000 g of the conventional granule of Example 5, 700 g of 10% ethanol solution of white beeswax was spray-coated to make a controlled-release granule. The resulting granule showed about 72% dissolution at 5 hrs.

Example 12

To 500 g of the conventional granule of Example 5, 450 g of 3% ethanol solution of Shellac was sprayed to form a controlled-release granule. The resulting granule showed about 68% dissolution at 5 hrs.

Example 13

550 g of the conventional granule of Example 5 was converted to enteric-coated granules by spraying 500 g of 5% ethanol solution of HPMCP ®, and the resulting granule exhibited about 5% dissolution in the First Medium at 1 hr. and about 70% dissolution in the Second Medium at the subsequent 3 hrs.

Example 14

An enteric-coated crystal of KC-404 was prepared by spray-coating 1350 g of 3.2% ethanol solution of Eudragit L ® onto 300 g of KC-404 crystal having a diameter of 0.18–0.42 mm. The resulting crystal showed about 4% dissolution in the First Medium at 1 hr. and about 70% dissolution in the Second Medium at the subsequent 4 hrs.

Example 15

To 2800 g of the conventional granule of Example 5, 1400 g of 3% ethanol solution of ethylcellulose was sprayed to produce a controlled-release granule. The resulting granule showed about 20% dissolution in the First Medium at 2 hrs. and about 70% dissolution at 5 hrs.

Example 16

Figure 5:
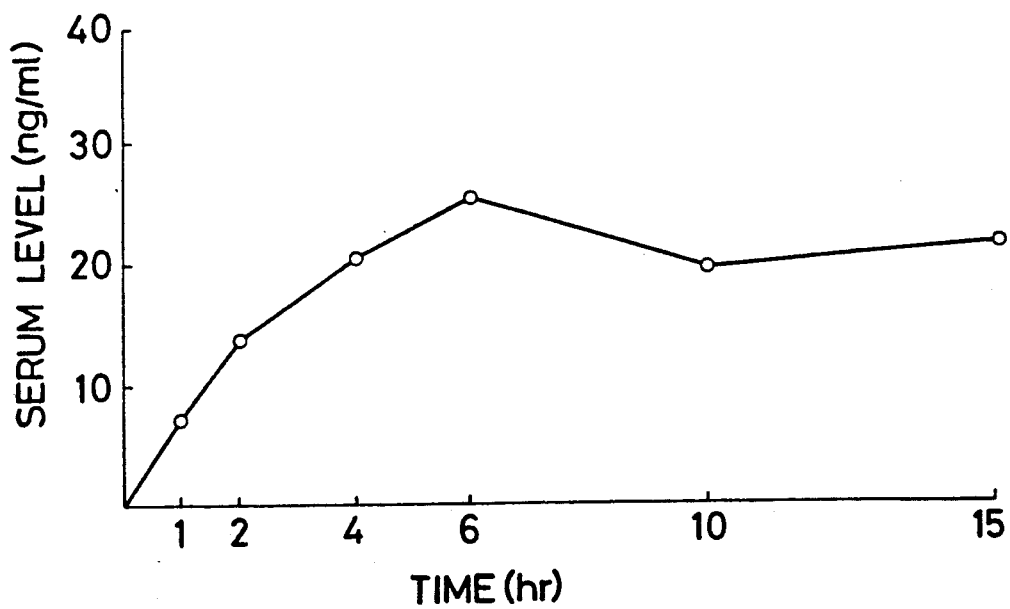
FIG. 5 shows the serum level profile in healthy volunteers who received suppositories containing 20 mg of KC-404, which were prepared as in Example 16.

0.51 g of KC-404 was dissolved in 49.5 g of Witepsol ®W-35, which had been preheated and melted at 45° C. Each 1.95 g of the resulting melted mass was cooled down to room temperature in a plastic container for suppositories containing 20 mg of KC-404. The serum level in healthy volunteers resulting from this suppository displayed a gradual increase for 6 hrs. after the dose was given and maintained the level up to 15 hrs. after the dose was given (FIG. 5).

Example 17

24.99 kg of Witepsol ® W-35 was melted at 60° C. and then 391 g of KC-404 was dissolved therein. The resulting melted mass was injected into a plastic container for suppositories by an automated manufacturing machine for suppositories, maintaining a temperature of about 33° C., and then solidified by cooling at 20°–18° C. and sealed. Each suppository contained 20 mg of KC-404, weighing 1.3 g.

Example 18

24.96 kg of Witepsol ® W-35 was melted at about 60° C. and then 194 g of KC-404 was dissolved therein. The resulting melted mass was injected into a plastic container for suppositories by an automated manufacturing machine for suppositories, keeping the temperature at about 37° C., and then solidified at 20°–18° C. and sealed. Each suppository contained 10 mg of KC-404, weighing 1.3 g.

Example 19

2 g of KC-404 was dissolved in 78 g of Witepsol ® H preheated at about 43° C., and injected into a plastic container for suppositories to be 0.8 g as a net weight, and then solidified at ambient temperature.

Example 20

2 g of KC-404 was dissolved in 78 g of Witepsol ® E preheated at about 55° C., and the resulting melted mass was injected into a plastic container for suppositories to be 0.8 g as a net weight, and then solidified at ambient temperature.

What is claimed is:

1. A pharmaceutical composition comprising a blend of:
   (a) a first component having a core of a pharmaceutically acceptable carrier and 3-isobutyryl-2-isopropylpyrazolopyridine and a first coating on said core capable of controllably releasing the 3-isobutyryl-2-isopropylpyrazolopyridine in the stomach and intestines; and
   (b) a second component comprising a core of a pharmaceutically acceptable carrier and 3-isobutyryl-2-isopropylpyrazolopyridine, a first coating on said core capable of controllably releasing the 3-isobutyryl-2-isopropylpyrazolopyridine in the stomach and intestines, and a second enterosoluble coating on said first coating capable of controllably releasing the 3-isobutyryl-2-isopropylpyrazolo [1,5-a] pyridine only into the intestinal tract;
   wherein the weight granule equivalent of said second component to said first component is from about 2:1 to 3:1 and the amount of 3-isobutyryl-2-isopropylpyrazolopyridine in the preparation is a vasodilating or bronchodilating effective amount.

2. The composition of claim 5 wherein the first coating is a copolymer of ethyl methacrylate and trimethylacrylethylammonium chloride.

3. The composition of claim 1 wherein the second coating is a copolymer of methyl methacrylate and methacrylate.

4. The composition of claim 1 wherein the weight granule equivalent of the second component to the first component is 2:1.

5. The composition of claim 1 wherein the weight granule equivalent of the second component to the first component is 3:1.

6. The composition of claim 1 wherein the core comprises a granule of a pharmaceutically available excipient and a layer of 3-isobutyryl-2-isopropylpyrazolopyridine thereon.

7. The composition of claim 1 wherein the amount of 3-isobutyryl-2-isopropylpyrazolopyridine is from about 10 to 20 milligrams.

8. A method for preparing the composition of claim 1 comprising:
   (a) preparing a granule of a pharmaceutically available excipient, coating the granule with a layer of 3-isobutyryl-2-isopropylpyrazolopyridine, and coating the 3-isobutyryl-2-isopropylpyrazolopyridine layer with said first coating to form said first component in particulate form;
   (b) coating a fraction of the first component particles with the second coating to form said second component in particulate form; and
   (c) blending particles of the first and second components in a ratio from about 1:2 to 1:3.

9. A method for effecting a vasodilating or bronchodilating action in a human subject while avoiding nausea or vomiting side effects in said subject, said method comprising orally administering to the human subject the composition of claim 8 so as to increase the serum concentration of the 3-isobutyryl-2-isopropylpyrazolopyridine to a level sufficient to exert a vasodilating or bronchodilating effect at a serum level concentration rate increase sufficiently low so as to avoid nausea or vomiting.

* * * * *